US00PP26268P2

(12) United States Plant Patent
Rijnbeek

(10) Patent No.: US PP26,268 P2
(45) Date of Patent: Dec. 22, 2015

(54) ***AGAPANTHUS* PLANT NAMED 'LITTLE DUTCH BLUE'**

(50) Latin Name: *Agapanthus africanus*
Varietal Denomination: Little Dutch Blue

(71) Applicant: Anthonius Phillipus Maria Rijnbeek, Boskoop (NL)

(72) Inventor: Anthonius Phillipus Maria Rijnbeek, Boskoop (NL)

( * ) Notice: Subject to any disclaimer, the term of this patent is extended or adjusted under 35 U.S.C. 154(b) by 191 days.

(21) Appl. No.: 13/998,441

(22) Filed: Oct. 31, 2013

(51) Int. Cl.
*A01H 5/02* (2006.01)

(52) U.S. Cl.
USPC ..... Plt./398

(58) Field of Classification Search
USPC ..... Plt./398
See application file for complete search history.

*Primary Examiner* — Anne Grunberg
(74) *Attorney, Agent, or Firm* — C. A. Whealy

(57) ABSTRACT

A new and distinct cultivar of *Agapanthus* plant named 'Little Dutch Blue', characterized by its compact and upright plant habit; numerous star-shaped flowers with violet blue-striped flowers arranged on upright and strong scapes; continuous flowering throughout the summer; and good garden performance.

2 Drawing Sheets

Botanical designation: *Agapanthus africanus.*
Cultivar denomination: 'LITTLE DUTCH BLUE'.

BACKGROUND OF THE INVENTION

The present invention relates to a new and distinct cultivar of *Agapanthus* plant, botanically known as *Agapanthus africanus* and hereinafter referred to by the name 'Little Dutch Blue'.

The new *Agapanthus* plant is a naturally-occurring whole plant mutation of *Agapanthus africanus* 'Blue Heaven', disclosed in U.S. Plant Pat. No. 14,989. The new *Agapanthus* plant was discovered as a single flowering plant from within a population of plants of 'Blue Heaven' in grown in a controlled greenhouse environment in Boskoop, The Netherlands in June, 2010.

Asexual reproduction of the new *Agapanthus* plant by divisions in a controlled environment in Boskoop, The Netherlands since the autumn of 2010 has shown that the unique features of this new *Agapanthus* plant are stable and reproduced true to type in successive generations.

SUMMARY OF THE INVENTION

Plants of the new *Agapanthus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Little Dutch Blue'. These characteristics in combination distinguish 'Little Dutch Blue' as a new and distinct *Agapanthus* plant:

1. Compact and upright plant habit.
2. Numerous star-shaped flowers with violet blue-striped flowers arranged on upright and strong scapes.
3. Continuous flowering throughout the summer.
4. Good garden performance.

Plants of the new *Agapanthus* differ primarily from plants of the mutation parent, 'Blue Heaven', primarily in plant size. In side-by-side comparisons conducted in Boskoop, The Netherlands, plants of the new *Agapanthus* were less than half the height of plants of 'Blue Heaven'.

Plants of the new *Agapanthus* can be compared to plants of *Agapanthus* 'Peter Pan', not patented. In side-by-side comparisons conducted in Boskoop, The Netherlands, plants of the new *Agapanthus* and 'Peter Pan' differed in the following characteristics:

1. Leaves of plants of the new *Agapanthus* were longer and not as blue in color as leaves of 'Peter Pan'.
2. Plants of the new *Agapanthus* flowered for a much longer period of time during the summer than 'Peter Pan'.

BRIEF DESCRIPTION OF THE PHOTOGRAPHS

The accompanying colored photographs illustrate the overall appearance of the new *Agapanthus* plant showing the colors as true as it is reasonably possible to obtain in colored reproductions of this type. Colors in the photographs may differ slightly from the color values cited in the detailed botanical description which accurately describe the colors of the new *Agapanthus* plant.

The photograph on the first sheet comprises a side perspective view of a typical flowering plant of 'Little Dutch Blue' grown in a container.

The photograph on the second sheet is a close-up view of a typical inflorescence of 'Little Dutch Blue'.

DETAILED BOTANICAL DESCRIPTION

The aforementioned photographs and following observations, measurements and values describe plants grown during the late spring and early summer in 17-cm containers in a greenhouse in Boskoop, The Netherlands and under cultural practices typical of commercial *Agapanthus* production. During the production of the plants, day temperatures ranged from 15° C. to 24° C. and night temperatures ranged from 5° C. to 18° C. Plants were one year old when the photographs and description were taken. In the following description, color references are made to The Royal Horticultural Society Colour Chart, 2007 Edition, except where general terms of ordinary dictionary significance are used.

Botanical classification: *Agapanthus africanus* 'Little Dutch Blue'.

Parentage: Naturally-occurring whole plant mutation of *Agapanthus africanus* 'Blue Heaven', disclosed in U.S. Plant Pat. No. 14,989.

Propagation:

*Type*.—By tissue culture.

*Time to produce a rooted plant, summer*.—About six weeks at temperatures about 18° C.

*Root description*.—Medium in thickness, slightly fibrous to fleshy; yellow white to greyed orange in color.

*Rooting habit*.—Moderate branching; medium density.

Plant description:

*Plant form and growth habit*.—Herbaceous flowering perennial plant; compact and upright plant habit and strong upright flower scapes; leaves and flowering stems basal; low to moderately vigorous growth habit.

*Plant height* (*soil level to top of foliar plane*).—About 12.6 cm,

*Plant height* (*soil level to top of floral plane*).—About 33.4 cm.

*Plant width* (*spread*).—About 25.9 cm.

Leaf description:

*Arrangement and appearance*.—Leaves arranged in a basal rosette with about six leaves per rosette; leaves distichous, simple and sessile.

*Leaf length*.—About 16.2 cm.

*Leaf width*.—About 1.1 cm.

*Shape*.—Ligulate.

*Apex*.—Narrowly acute.

*Base*.—Cuneate.

*Margin*.—Entire.

*Texture, upper and lower surfaces*.—Smooth, glabrous; thick and leathery.

*Venation pattern*.—Parallel.

*Color*.—Developing leaves, upper and lower surfaces: Close to between 137B and 143A. Fully expanded leaves, upper surface: Close to N137B; venation, close to N137B. Fully expanded leaves, lower surface: Close to 137B; venation, close to 143A.

Flower description:

*Flower type and flowering habit*.—Single star-shaped flowers arranged in terminal umbels supported by strong upright scapes; flowers face mostly outwardly; umbels roughly hemispherical in shape; freely flowering habit with about 30 flowers developing per umbel.

*Fragrance*.—Faint, sweet.

*Natural flowering season*.—Plants being flowering about ten months after planting; long flowering period, flowering continuous from early summer to early autumn in The Netherlands.

*Postproduction longevity*.—Flowers last about one week the plant; flowers not persistent.

*Flower buds*.—Height: About 1.9 cm. Diameter: About 6 mm. Shape: Oblanceolate. Color: Close to between 93C and 94B; stripes, close to between 92D and NN155C.

*Inflorescence height*.—About 6.8 cm.

*Inflorescence diameter*.—About 9.5 cm.

*Flower diameter*.—About 3.8 cm.

*Flower depth*.—About 3.3 cm.

*Perianth*.—Quantity and arrangement: Typically six segments arranged in two whorls; lower 20% of the segments are fused into a narrow tube; upper free part of segments flaring outwardly. Segment length: About 3.2 cm. Segment width, inner whorl: About 9 mm. Segment width, outer whorl: About 7 mm. Segment lobe shape: Narrowly obovate. Segment apex: Broadly acute. Segment margin: Entire. Segment texture, upper and lower surfaces: Smooth, glabrous. Segment color: When opening, upper and lower surfaces: Close to 92B to 92D; towards the base, towards the margins and central longitudinal stripe, close to 94B. Fully opened, upper and lower surfaces: Close to 92B to 92D; towards the base and towards the margins, close to 92A; central stripe, close to 94B; color becoming closer to 94C with development.

*Peduncles* (*scapes*).—Length: About 29.5 cm. Diameter: About 3 mm to 5 mm. Aspect: Upright to about 15° from vertical. Strength: Strong. Texture: Smooth, glabrous. Color: Close to 143B.

*Pedicels*.—Length: About 1.7 cm. Diameter: About 1.5 mm. Aspect: Upright to horizontal from the peduncle axis. Strength: Strong. Texture: Smooth, glabrous. Color: Close to 143A.

*Reproductive organs*.—Stamens: Quantity per flower: Typically six. Filament length: About 2.3 cm. Filament color: Close to N88D; towards the base, close to 85D to lighter than 85D. Anther shape: Oblong; dorsifixed. Anther length: About 2 mm. Anther color: Close to 202B. Pollen amount: Moderate. Pollen color: Close to 152A. Pistils: Quantity per flower: One. Pistil length: About 2.2 cm. Style length: About 2.1 cm. Style color: Close to N88D; towards the base, close to 85D to lighter than 85D. Stigma shape: Narrowly clavate. Stigma color: Close to NN88D. Ovary color: Close to 150C.

*Seeds and fruits*.—Seed and fruit development have not been observed on plants of the new *Agapanthus*.

Disease & pest resistance: Plants of the new *Agapanthus* have not been noted to be resistant to pathogens and pests common to *Agapanthus* plants.

Garden performance: Plants of the new *Agapanthus* have been observed to have good garden performance and to tolerate rain, wind, high temperatures about 40° C. and to be hardy to USDA Hardiness Zone 8.

It is claimed:

1. A new and distinct *Agapanthus* plant named 'Little Dutch Blue' as illustrated and described.

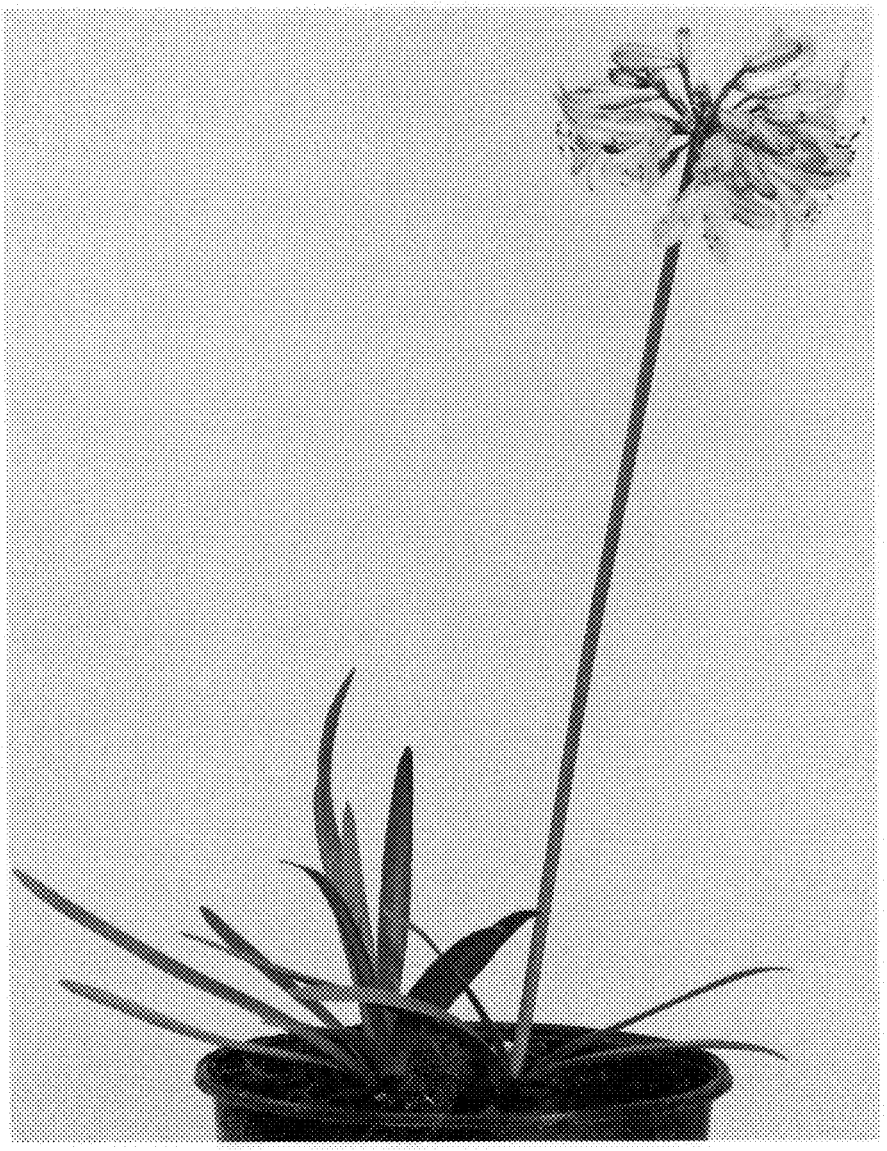

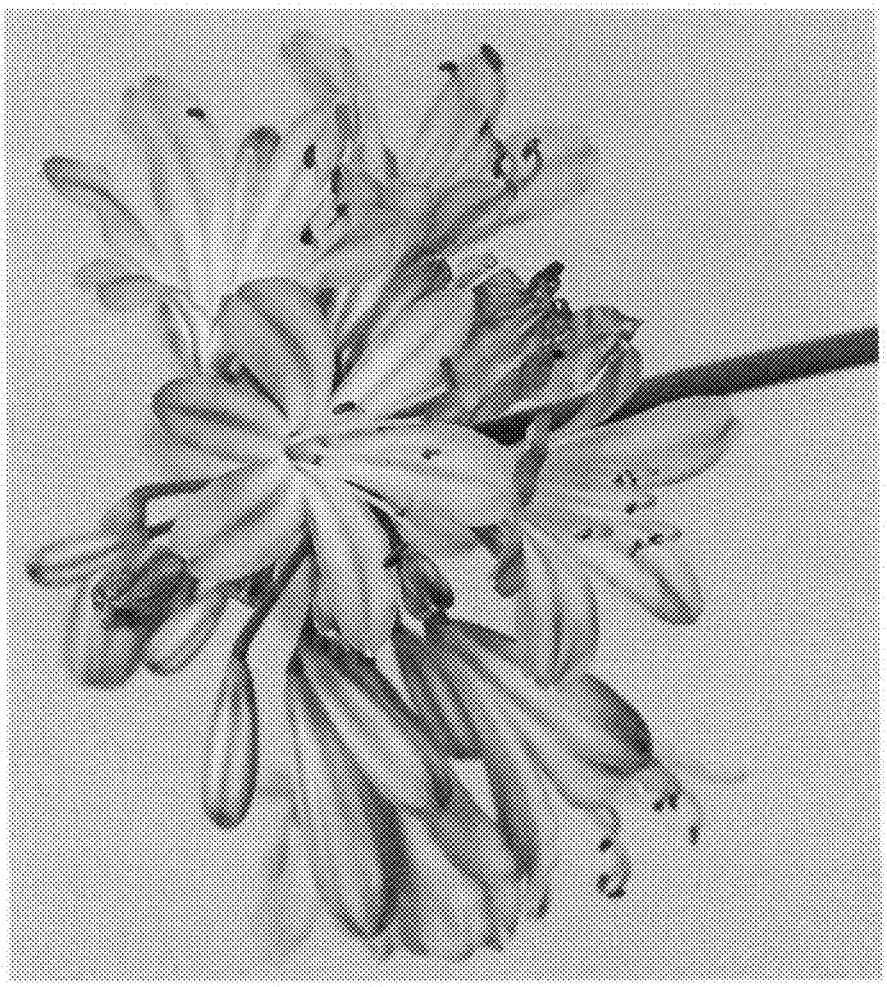

* * * * *